United States Patent [19]

Bailey et al.

[11] Patent Number: 4,771,001

[45] Date of Patent: * Sep. 13, 1988

[54] PRODUCTION OF LACTIC ACID BY CONTINUOUS FERMENTATION USING AN INEXPENSIVE RAW MATERIAL AND A SIMPLIFIED METHOD OF LACTIC ACID PURIFICATION

[75] Inventors: Richard B. Bailey, Cupertino, Calif.; Dilip K. Joshi, Kalamazoo, Mich.; Stephen L. Michaels, Newton, Mass.; Richard A. Wisdom, Foster City, Calif.

[73] Assignee: Neurex Corp., Menlo Park, Calif.

[ * ] Notice: The portion of the term of this patent subsequent to Oct. 6, 2004 has been disclaimed.

[21] Appl. No.: 910,949

[22] Filed: Sep. 24, 1986

Related U.S. Application Data

[63] Continuation-in-part of Ser. No. 844,819, Mar. 27, 1986, Pat. No. 4,698,303, which is a continuation-in-part of Ser. No. 702,472, Feb. 15, 1985, abandoned, and a continuation-in-part of Ser. No. 687,189, Dec. 28, 1984, abandoned.

[51] Int. Cl.$^4$ .................. C12P 7/56; C07C 59/08; A23C 21/02

[52] U.S. Cl. ..................... 435/139; 426/43; 426/41; 435/253; 435/813; 435/853; 435/885; 435/854; 435/856; 562/589

[58] Field of Search .............. 426/34, 41, 42, 43, 426/583, 271; 562/589, 580, 513; 435/139, 253, 212, 219, 267, 272, 220, 223, 226, 813, 856, 853; 210/607, 637-639, 650-651

[56] References Cited

U.S. PATENT DOCUMENTS

| | | |
|---|---|---|
| 1,540,951 | 6/1925 | Reichel et al. . |
| 1,704,458 | 3/1929 | Brahm . |
| 2,539,472 | 1/1951 | Ratchford et al. . |
| 2,710,880 | 6/1955 | Filachione et al. . |
| 2,838,443 | 6/1958 | Gillespie et al. . |
| 2,885,436 | 5/1959 | Wangel . |
| 3,036,918 | 6/1962 | Wingerd . |
| 3,284,495 | 11/1966 | Vogt et al. . |
| 3,944,606 | 3/1976 | Rieger et al. . |
| 4,001,437 | 1/1977 | Jaeggi et al. . |
| 4,016,295 | 4/1977 | Burrows et al. . |
| 4,036,999 | 7/1977 | Grindstaff .................. 426/41 |
| 4,275,234 | 6/1981 | Baniel et al. ................ 562/584 |
| 4,291,007 | 9/1981 | Baniel . |
| 4,334,095 | 6/1982 | Baniel . |
| 4,364,962 | 12/1982 | Tachenhagen et al. .......... 426/42 |
| 4,427,658 | 1/1984 | Maubois et al. . |
| 4,444,881 | 4/1984 | Urbas ........................ 435/139 |
| 4,500,549 | 2/1985 | Crossman . |
| 4,529,611 | 7/1985 | Uiterwaal . |

FOREIGN PATENT DOCUMENTS 01104 3/1984 PCT Int'l Appl. .

OTHER PUBLICATIONS

Wennersten, *J. Chem. Tech. Biotechnol.* 33B, 85-94 (1983).
Ricker et al., *J. Separ. Proc. Technol.* 1, 23-30, (1980).
Mitchell et al., *J. Dairy Sci.* 66, 712-718, (1983).

*Primary Examiner*—Raymond N. Jones
*Assistant Examiner*—Marianne M. Cintins
*Attorney, Agent, or Firm*—Flehr, Hohbach, Test, Albritton & Herbert

[57] ABSTRACT

The disclosure describes a method for producing lactic acid from carbohydrate-containing media by continuous fermentation utilizing particular methods of media pretreatment, cell-recycle fermentation, fermentation broth acidification, and lactic acid separation.

21 Claims, 2 Drawing Sheets

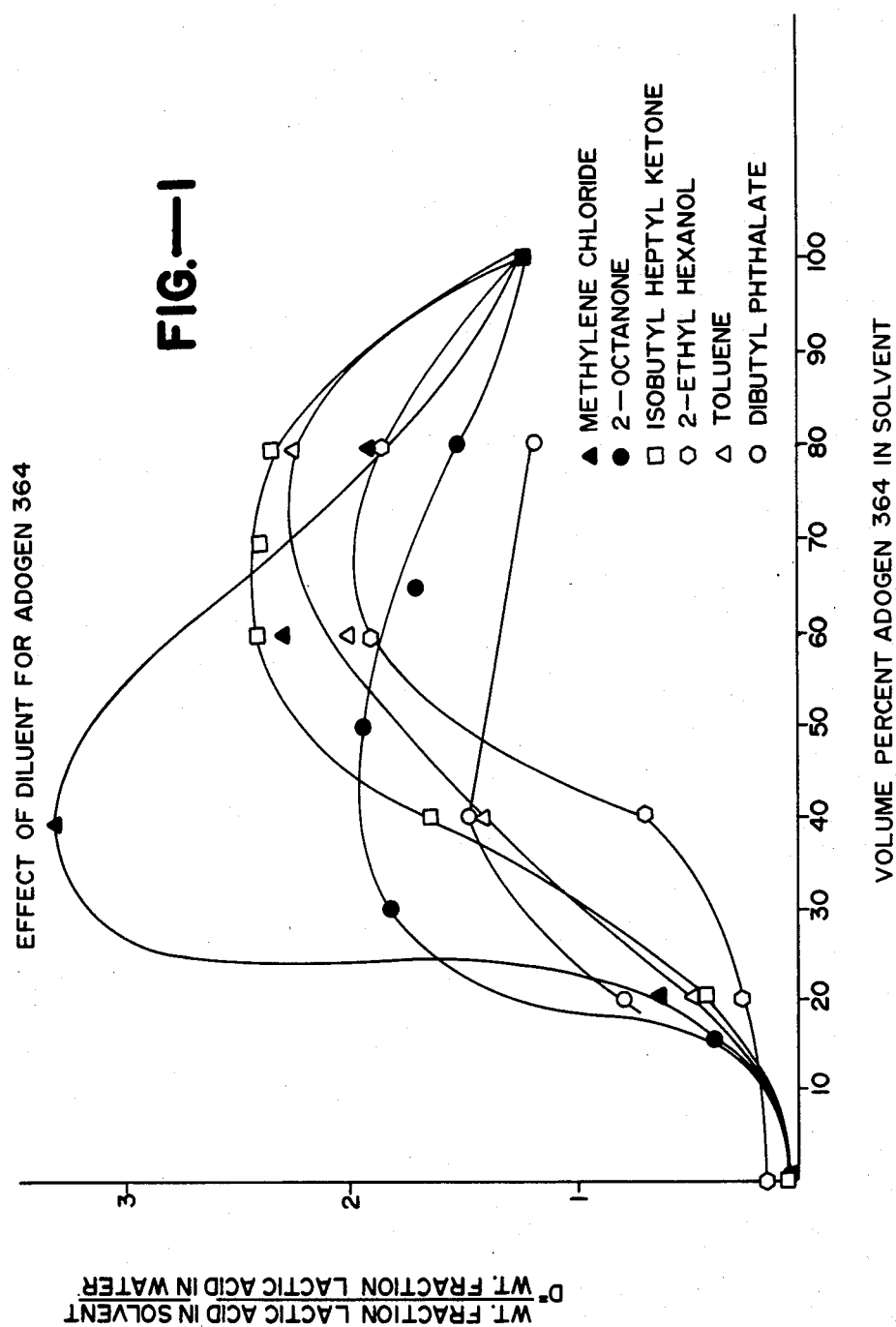

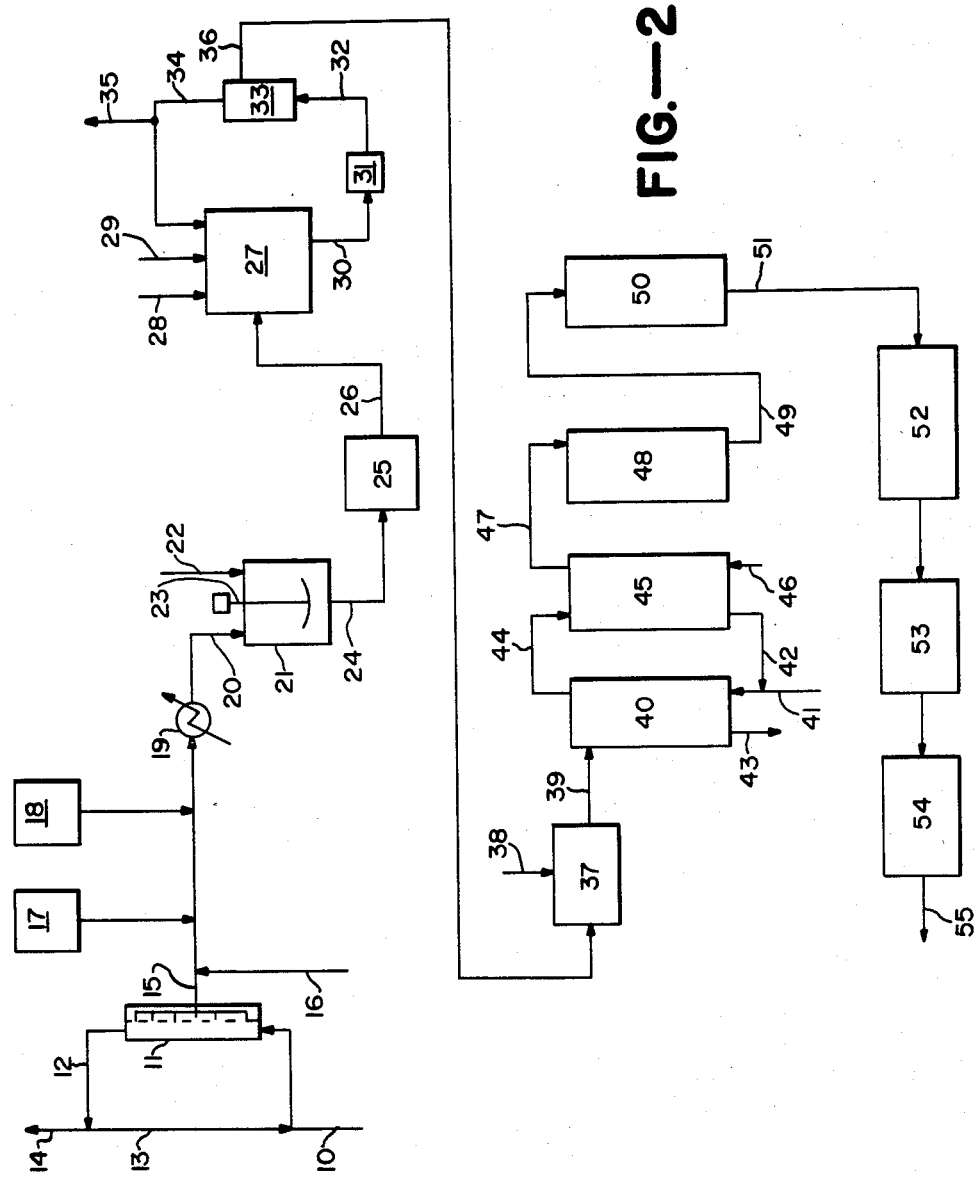
FIG.—2

PRODUCTION OF LACTIC ACID BY CONTINUOUS FERMENTATION USING AN INEXPENSIVE RAW MATERIAL AND A SIMPLIFIED METHOD OF LACTIC ACID PURIFICATION

This is a continuation-in-part of copending Ser. No. 844,819, filed Mar. 27, 1986, now U.S. Pat. No. 4,698,303 which in turn is a continuation-in-part of Ser. No. 702,472, now abandoned filed Feb. 15, 1985 and a continuation-in-part of copending Ser. No. 687,189, filed Dec. 28, 1984, now abandoned, all commonly assigned herewith.

The present invention is directed to the production of lactic acid from a continuous fermentation process using whey permeate as the raw material.

BACKGROUND

Lactic acid is a commodity biochemical sold in bulk and as a series of specialty derivatives into a competitive market highly sensitive to production costs. Currently, lactic acid is manufactured by synthetic and fermentative methods for use in food manufacturing, pharmaceuticals, leather tanning, metal pickling, and as a starting material in specialized chemical processes. Fermentations involving the production of lactic acid usually involve the conversion of monosaccharides such as glucose, fructose, galactose, or disaccharides such as sucrose or lactose into lactic acid. Certain homofermentative strains producing only lactic acid as a product have been used, such as *Lactobacillus delbrueckii, L. casei, L. acideophilus, and L. bulgaricus*. *L. delbrueckii* consumes either sucrose, glucose or fructose, but does not consume lactose. The other three species consume lactose and galactose in addition to the other sugars. However, to improve the efficiency and cost of lactic acid production by fermentative methods, there is a need to find low-cost, high-nutrient media, and to develop cheaper more efficient production systems.

Heat-stable, food-grade lactic acid requires a high degree of purity. Thus, it is not obvious that the production of lactic acid by fermentation of a low-cost, high-nutrient media will result in an economical and simple process for the production of heat-stable lactic acid.

The present invention provides a combination of a continuous fermentation technology utilizing an industrial waste byproduct stream (e.g, cheese whey permeate) as the raw material and of a solvent extraction recovery process allows for the production of lactic acid at a cost below those associated with conventional manufacturing methods, while meeting quality standards. The process is applicable to the production of L(+), D(−), or L(+)D(−) racemic lactic acid. Thus, the term lactic acid will refer to all three of the cited forms.

Continuous high productivity bioreactors may be used to reduce the cost of fermentation-based processes. One such bioreactor is the retained-cell bioreactor (i.e., cell-recycle fermenter) which is a special example of a chemostat (CSTR) fermenter in which increased volumetric productivities are obtainable by continuously separating biomass from the product stream and recycling the biomass to the fermenter. Cross-flow microfiltration or ultrafiltration modules or centrifugation may be used to effect this separation. However, the economic advantage of any continuous process is highly dependent upon a long operating time relative to the batch process. Thus, for the successful operation of a retained-cell bioreactor based on cross-flow filtration, it is critical to minimize such problems as the fouling associated with solutes, especially proteins, which are found in the preferred raw material, such as cheese whey permeate.

Cheese whey permeate, which contains about 5% lactose, is an excellent raw material for lactic acid production because it is a domestic sugar source whose price is competitive with current world sugar prices. The large volumes of whey currently discarded around the U.S. are ample to support the total world lactic acid market volume. Whey proteins are not useful for this invention but may be recovered for sale as high value whey protein concentrate prior to fermentation of the whey permeate to lactic acid. Many cheese manufacturers recover the whey protein concentrate using ultrafiltration, a commercially available technique for removing large molecular weight proteins (greater than 10,000 daltons). However, in practice, this unit operation only recovers about 80% of the whey proteins, with the remainder passing into the whey permeate stream.

Sweet cheese whey permeate is preferred as a raw material. However, the presence of these residual proteins in the whey permeate makes its use as a fermentation feedstock problematical. The residual milk proteins present in cheese whey precipitate upon heating and upon contact with high salt concentrations or organic solvents. This can result in fouled heat transfer surfaces and mass transfer equipment, making the necessary sterilization and recovery operations difficult and expensive. Also, thermal sterilization of whey produces condensation products of proteins which inhibit bacterial growth and lactic acid productivity. Furthermore, the ability of some lactic acid-producing microorganisms to hydrolyze large proteins and peptides is limited which means the proteins in cheese whey may contribute little nutrient value for cell growth. Thus, additional nutrients must be added to a whey-based fermentation medium which adds cost to the final product.

Therefore, it would be desirable to filter sterilize the whey permeate. However, surprisingly, it was found that the proteins remaining in the whey permeate also fouled the sterile filters to an extent that impeded filtration.

This problem of precipitable proteins is particularly relevant to the continuous fermentation and recovery technology described herein. To overcome this problem, the present invention provides a protease treatment for whey permeate that improves upon current technology by allowing longer term operation of the cell-recycle fermenter since it minimizes membrane fouling due to proteinaceous material. A second benefit of this treatment is that the proteins are proteolyzed to amino acids that can subsequently be used as nutrients by the lactic acid-producing bacteria. A third benefit is that amino acids, as opposed to non-proteolyzed proteins, will not interfere with the recovery procedure described herein.

As cited above, the principle source of sugar in whey permeate is lactose at a concentration of about 5%. The volumetric productivity of a batch fermentation using whey permeate as a source of sugar is very low since there is only a short period of fermentation at a high cell concentration before all the lactose is utilized.

Raw materials other than whey permeate may be utilized as starting materials in the process according to the present invention. Any fermentation medium containing at least one of a variety of carbohydrates may be used, such as, glucose, sucrose (such as that in molasses), fructose, maltose, cellobiose, galactose and xylose. Fermentation media containing at least one of these carbohydrates typically also contain one or more of the following: yeast extract, protein hydrolysate (such as, peptones or tryptones), corn steep liquor, and salts of calcium, magnesium, potassium and phosphate.

The concentration of each component of a suitable fermentation medium for lactic acid production is determined by methods familiar to those skilled in the art. For instance, a suitable fermentation medium could contain 50 grams sucrose per liter, 10 grams Bacto-tryptone per liter, 1 gram monobasic potassium phosphate per liter, 0.5 grams magnesium sulfate per liter, 0.1 grams calcium chloride per liter, and 1 gram yeast extract per liter. Any carbohydrate from the above list could be effectively substituted for sucrose in this medium.

If using a fermentation medium as a starting material, other than lactose-containing whey permeate, in accordance with the invention, it will be recognized by those skilled in the art that a protein hydrolysis pretreatment is not essential. Thus, in cases of such starting materials, the fermentation medium may usually be directly subjected to the fermentation microorganism. In a cell-recycle fermenter (e.g, U.S. Pat. No. 3,472,765), the cells are continuously separated from the product stream and returned to the fermenter. Thus, cells that have been grown are not discarded after a single fermentation but are reused. Indeed, it is possible to obtain cell concentrations in the fermenter many times greater than those obtainable in batch fermentation. Therefore, there are several advantages to using a cell-recycle fermenter over a batch fermenter for the fermentation of whey permeate: (1) The long lead times associated with growing the cells from an initial low concentration is not required once steady state has been reached. (2) Much higher cell concentrations (up to 100 grams per liter dry weight) can be reached than those obtainable using batch fermentation. This translates into a greater rate of lactic acid production per unit volume of fermenter. (3) The fermentation is run continuously, allowing product to be pumped downstream to the continuous purification operations without the need for holding tanks. In addition, the fermentation can readily be automated to give a less variable process stream, and there is no down time associated with cleaning and sterilizing the fermenter.

As one aspect of this invention, the cell-recycle fermenter provides other advantages specific to the process for the conversion of whey permeate to heat-stable, food-grade lactic acid: Through suitable choice of fermentation conditions, it is possible to reduce the level of lactose in the product stream to less than 0.01%, while still maintaining economically attractive volumetric productivities. In addition, the fermentation provides this level of performance despite variations of greater than 10% in the concentration of lactose in the waste whey permeate stream. These characteristics are important to the overall process as it is necessary to reduce the residual level of lactose in the lactic acid product stream to as low a level as possible so as to minimize color formation during heating, a principle definition of heat-stable, food-grade lactic acid.

In order to obtain heat-stable lactic acid from the cell-recycle fermentation broth, a simple and inexpensive recovery process is required that selects for lactic acid and against residual carbohydrates, peptides, and color bodies. Such a process, centered on solvent extraction technology, is described herein.

Previous patents (e.g, U.S. Pat. Nos. 3,944,606, 4,275,234, 4,334,095) have disclosed methods for recovering organic acids from aqueous solutions comprising an extraction step whereby the aqueous solution is contacted with a water-immiscible organic solvent containing a secondary, or tertiary amine having at least 20 carbon atoms; the subsequent back-extraction step uses either a temperature or pH differential as the driving force. Forward extraction processes have previously shown that the coefficient of distribution for lactic acid in the water-immiscible extraction liquid is a linear function of increasing the concentration of amine in the organic solvent.

Surprisingly, the present invention provides a method whereby increasing the concentration of amine in the solvent beyond a certain point does not result in a linear increase in the coefficient of distribution of lactic acid: A solution composed of 100% amine does not give the best distribution coefficient for lactic acid. That is, addition of the proper amount of solvent gives a pronounced synergistic effect, depending on the combination of amine and solvent utilized.

The choice of solvent is highly relevant to another feature of this process. Specifically, the invention provides for a high degree of separation between lactic acid and residual sugars during the solvent extraction procedure. The solvents provided are highly selective to lactic acid and reject all the residual sugars in the raffinate. Complete removal of sugars by this process results in heat-stable lactic acid.

Another important aspect of this invention is the preparation of the fermentation broth for extraction. Previous methods of acidification have involved the addition of mineral acids such as sulfuric or hydrochloric. Addition of mineral acids or salts, however, is undesirable since anions from the acid and salts are coextracted with the desired lactic acid.

Thus, an advantage of the invention is that acidification of the fermentation broth may be accomplished by passing the aqueous solution through an appropriate cation exchange resin in the hydrogenated form to achieve the desired pH range. This methodology is particularly necessary in conjunction with the extraction technology of this invention, since acidification by ion exchange has the advantages of removing undesired cations and some color bodies from the broth and of eliminating the addition of anions, all of which might be coextracted with the lactic acid during the solvent extraction step. Thus, acidification by ion exchange will lead to a less complicated and less expensive recovery procedure that will be more readily convertible into a continuous process.

It is the object of the invention to demonstrate a cost-effective fermentation-based process for the production of heat-stable (i.e., food-grade) lactic acid.

To this end, it is an object of the present invention to provide a method for preparing cheese whey permeate for use as a low cost fermentation medium for lactic acid production.

Another object of the present invention is to provide processed whey permeate which may be subjected to filter sterilization, heat sterilization, solvent extraction, or other refining processes without precipitation of proteins.

It is a further object to provide a protease treatment for whey permeate which improves long term operation of a filtration-based cell-recycle fermentation by minimizing fouling of the filtration membrane due to proteinaceous material.

A further object is to provide proteins which are proteolyzed to amino acids that may be subsequently used as nutrients by lactic acid-producing bacteria.

Another object is to provide a method whereby amino acids, as opposed to non-proteolyzed proteins, will not interfere with the recovery procedure.

A further object of the present invention is to utilize a continuous cell-recycle fermentation to obtain high cell densities, and, consequently, a high productivity of lactic acid over an extended period of time.

Another object of the present invention is to obtain a high conversion (approaching 100% of theoretical) of the lactose in whey permeate to lactic acid.

Another object of the present invention is to acidify the resultant fermentation broth without the addition of anions.

Another object of the present invention is to provide an improved method for recovering, purifying, and concentrating lactic acid from whole, centrifuged, or ultrafiltered fermentation broths containing lactic acid.

Another object of the present invention is to use mixed solvents to obtain solvent compositions that have high capacity for lactic acid.

It is a further object of the present invention to provide a method of recovering, purifying and concentrating lactic acid from fermentation broths without the use of temperature gradients.

These and other objects of the invention will be apparent from the following description of the preferred embodiments.

SUMMARY OF THE INVENTION

The invention provides a method for producing lactic acid by continuous fermentation. In a preferred embodiment, particular methods of whey permeate media pretreatment are utilized. More specifically, the invention provides a process for producing lactic acid from fermentation broth comprising the steps of (a) fermenting the broth with a lactic acid or lactic acid salt-producing microorganism in a fermentation zone, (b) continuously removing a product-containing broth from said zone, removing cells of said microorganism from said broth to form a cell-free product-containing stream and recycling said cells to said zone; (c) contacting said cell-free lactate-containing stream at an acidic pH with a water-immiscible liquid consisting essentially of trialkyl tertiary amines of at least 24 carbon atoms and a water-immiscible organic solvent, whereby lactic acid and lactic acid salt are extracted from said stream into a water-immiscible phase, said liquid characterized by a distribution coefficient in excess of 1.0 for lactic acid and lactic acid salt in said liquid versus water; (d) separating said water-immiscible liquid from the mixture formed in step (c); and (e) contacting said water-immiscible phase from step (d) with a material selected from the group consisting of aqueous ammonium hydroxide, solid alkalis, solid alkaline earth compounds, and aqueous non-homogenous suspensions of solid alkalis or solid alkaline earth compounds, whereby lactic acid and lactic acid salt are removed from said water-immiscible phase.

If the fermentation broth is whey permeate, the invention further provides a method of pretreatment of the whey comprising the steps of (1) providing the whey composition at an acidic pH from which a substantial portion of proteins having a molecular weight over 10,000 have been removed by ultrafiltration, (2) treating the composition from step (1) with a protease at a temperature in the range of 40° C. to 65° C. for a period sufficient to degrade proteins to smaller peptides and amino acids, such smaller peptides and amino acids characterized as being nonprecipitable under conditions of heat sterilization, increased salt concentration, or contact with organic solvents.

BRIEF DESCRIPTION OF THE DRAWINGS

FIG. 1 is a plot of the coefficients of distribution of lactic acid in several organic solvents as a function of concentration of tertiary amines (Adogen 364) in the solvent.

FIG. 2 is a flow sheet that depicts the process for production of heat-stable lactic acid according to the invention.

DESCRIPTION OF THE PREFERRED EMBODIMENTS

The present invention provides a method for preparing lactic acid using whey or other carbohydrate-containing media as a fermentation medium for lactate or lactic-acid producing microorganism fermentations. The wheys which may be processed according to the present invention include wheys which are by-products of the dairy industry. Wheys are normally formed in several ways, such as by the addition of acid to milk (to form acid whey), by the addition of rennet to milk (to form rennet whey), or by coagulation at neutral pH (to form sweet whey). Wheys may also be formed by the ultrafiltration of whole or nonfat milk. The composition of wheys may therefore vary depending upon the starting milk which is used and the cheese processing which is employed. However, all wheys contain in addition to lactose, minerals, fats, a certain amount of lactic acid, coagulant enzymes and a nitrogenous fraction comprising soluble milk proteins. Any of the whey by-products of the dairy industry may be used as a starting material for the present invention. The starting material to be used in the present invention will be provided in a form whereby a substantial portion of proteins having a molecular weight over 10,000 daltons will have been removed (i.e., by ultrafiltration). In some instances, no additional processing of the starting material will be required since dairy whey by-products are often ultrafiltered prior to disposal by the factory. However, if whole whey is to be utilized as a starting material, it must first be ultrafiltered by conventional means. Ultrafiltration will normally remove about 80% or more of the proteins having a molecular weight of over 10,000 daltons.

Raw materials other than whey permeate may be utilized as starting materials in the process according to the present invention. Any fermentation medium containing at least one of a variety of carbohydrates may be used, such as, glucose, sucrose (such as that in molasses), fructose, maltose, cellobiose, galactose and xylose. Fermentation media containing at least one of these carbohydrates typically also contain one or more of the following: yeast extract, protein hydrolysate (such as, peptones or tryptones), corn steep liquor, and salts of calcium, magnesium, potassium and phosphate.

The concentration of each component of a suitable fermentation medium for lactic acid production is determined by methods familiar to those skilled in the art. For instance, a suitable fermentation medium could contain 50 grams sucrose per liter, 10 grams Bacto-tryptone per liter, 1 gram monobasic potassium phosphate per liter, 0.5 grams magnesium sulfate per liter, 0.1 grams calcium chloride per liter, and 1 gram yeast extract per liter. Any carbohydrate from the above list could be effectively substituted for sucrose in this medium.

If using a fermentation medium as a starting material, other than lactose-containing whey permeate, in accordance with the invention, it will be recognized by those skilled in the art that a protein hydrolysis pretreatment is not essential. Thus, in cases of such starting materials, the fermentation medium may usually be directly subjected to the fermentation microorganism.

For the preferred acid protease treatment of whey described in this invention, the ultrafiltered whey will be adjusted to a pH in the range of 2.0 to 5.0, preferably pH 4.0. This will usually be done by the addition of mineral or organic acids since most wheys have a pH above this range. Mineral acids such as sulfuric or hydrochloric may be used, or organic acids such as citric, acetic or lactic. In the present invention lactic acid is the preferred organic acid, and sulfuric acid is the preferred mineral acid.

After adjustment of the pH, the whey composition will be treated with a protease at a temperature in the range of 40° C. to 65° C., preferably at 60° C. Treatment of the whey with the protease may be done by conventional means, either continuously or by batch processing. The whey will be contacted with a protease in a reaction zone at the desired temperature and pH with the reaction being continued until the protease has degraded the proteins to lower molecular weight peptides and amino acids which will not precipitate with incubation in the presence of cold 5% trichloroacetic acid. These lower molecular weight peptides and amino acids will then not be precipitated by heat sterilization, increase of salt concentration, or contact with organic solvents. Furthermore, the degradation of the large proteins to peptides and amino acids enhances the nutritional value of the whey to the microorganism and in most instances obviates the necessity of adding amino acids as a nutritional supplement to the medium.

Proteolysis of whey permeate by the method described herein results in an improved fermentation medium which will support the growth of all lactic acid bacteria tested. Surprisingly, the processed whey does not necessarily need to be further supplemented with vitamins, amino acids, or complex mixtures of these compounds such as yeast extract or corn steep liquor.

In the event that additional complex nutrients are desired to support high density cell growth, it is a further object of this invention that they may be added to the whey permeate before protease treatment. Thus, any large molecular weight proteins present in the complex nutrient source would be simultaneously hydrolyzed with the whey proteins. This is especially valuable when lower cost but more poorly refined nutrient sources such as corn steep liquor or yeast extract are added.

Many commercial protease enzyme preparations will satisfactorily hydrolyze when proteins to satisfy the intent of this invention. Acid proteases are preferable since incubation at the low pH required for their optimum activity minimizes problems of growth of contaminating microorganisms.

The preferred acid protease to be used is commercially avaiable from Miles as MILEZYME AFP. However, other commercially available protease enzymes work satisfactorily such as Miles' TAKAMINE FUNGAL PROTEASE, HT-PROTEOLYTIC, and TAKAMINE PANCREATIN 4 N.F. None of the latter enzymes have pH optima as low as MILEZYME AFP, however, and thus the whey is more prone to become contaminated during the prolonged incubation period needed to achieve hydrolysis. Normally the whey will be incubated with the protease for a period of four to twelve hours, depending upon the ratio of enzyme to protein.

The protease enzyme-to-whey protein ratio determines the length of time necessary to achieve the needed amount of hydrolysis. A minimum of 40 enzyme units (Miles' Spectrophotometric Acid Protease Unit) per gram of whey protein was sufficient to give the necessary amount of protein hydrolysis within 8 hours. A value of 0.02 grams of MILEZYME AFP 2000 per liter of whey permeate was routinely used.

Protein hydrolysis was determined to be complete when all of the protein was soluble in a solution of 5% trichloroacetic acid (TCA) which had been kept on ice for 30 minutes. Generally, when the whey protein was 85% to 90% hydrolyzed, subsequent heat sterilization did not result in precipitation. The "percent hydrolysis" was monitored by comparing the TCA-precipitable protein in a non-hydrolyzed control sample with the amount of TCA-precipitable protein found in the enzyme treated whey. Protein was quantified by using the Lowry method (Lowry, O.H., N.J. Rosebrough, A.L. Farr, and R.J. Randall. 1951. $J.$ $Biol.$ $Chem.$ 193:265–275), using beta-lactoglobulin as a standard.

The protease-digested whey will then be removed from the reaction zone and processed according to conventional methods for preparing a fermentation medium. Usually this further processing will include one or more of the following processes. Usually, a fermentation medium will be heat-sterilized prior to inoculation with a microorganism. The whey prepared according to the present invention is thus advantageous in that when subjected to heat sterilization conditions, there will be no precipitation of proteins. As an alternative sterilization method, the whey prepared according to the present invention may be sterile filtered through a 0.2 or 0.45 micron (absolute rating) sterilizing filter using commercially available equipment. Without the improvements specified by the present invention, the residual protein in the whey permeate quickly plugs these types of sterile filters making this method of sterilization too expensive to be of commercial use. Also, a typical processing step prior to inoculation of the medium is to adjust the pH to a range suitable for the growth of the microorganism being used by the addition of either an acid or a base.

In addition, the lactic acid recovery step described below is liquid-liquid extraction, in which an organic solvent which is immiscible with water is mixed with the fermentation broth. The lactic acid will be extracted into the organic solvent phase giving an immediate separation from the fermentation broth. With such a recovery step, the presense of protein in the fermentation broth presents a problem because the protein often precipitates upon contact with the organic solvent. The present invention circumvents this precipitation resulting in a cleaner separation.

It is therefore seen that the present invention affords a prcoess whereby whole, ultrafiltered whey by-products from the dairy industry may be utilized and processed into a fermentation medium for lactic acid-producing microorganisms, wherein the fermentation medium may be further processed by conventional methods without the undesirable precipitation of proteins which would foul reactors, pumps, lines, valves and other equipment.

The uses of the whey prepared according to the process of the present invention or other carbohydrate-containing fermentation media will be for microorganisms which produce lactic acid or lactic acid salt as a product. These microorganisms include various species of Lactobacillus, such as casei, acidophilus, bulgaricus, and so forth. The various conditions and cofactors, if necessary, required to conduct the fermentations are well known in the art.

In the cell-recycle system, a pump is used to continuously remove cell broth from the fermenter and pump it through a cross-flow microfiltration (or ultrafiltration) device(s). A cell-free permeate product stream is continuously removed from the cross-flow microfiltration device(s) and pumped downstream for purification. The concentrated cell broth is then returned to the fermenter. Protease-treated whey permeate feed is continuously pumped into the fermenter. A purge stream of broth may be used to continuously remove cells from the fermenter; this controls the build-up of cell mass. It also helps maintain a stable steady state conversion. Depending on the economics for the purge rate selected, the lactic acid may be recovered from this stream and combined with the main lactic acid permeate stream coming from the cross-flow microfiltration device(s). So as to maintain a constant volume in the fermenter, the rate of whey permeate feed should equal the rate of purge plus the rate of permeate product removal.

Optimal conditions for operation of the fermenter depend to a large extent on the organism selected for fermentation. The preferred organism of this invention is *L. casei*. This organism was selected due to its high specific productivity at high lactic acid concentrations and its high optimal temperature which decreases the risk of contamination during continuous fermentation. However other organisms, as previously described above, may also be used in this invention, and the fermentation controlled at conditions suitable for their optimal productivity.

For fermentation of *L. casei*, the temperature is maintained between 40° C. and 45° C. The pH is controlled between 5.0 and 6.5 through the addition of ammonium hydroxide. The fermentation is anaerobic; therefore, it is not necessary to supply air to the fermenter.

The feed and purge rates at which the fermentation is run depend to a large extent on the economics of the process and on the kinetics of the fermentation. Thus, at a low feed rate, the volumetric productivity of a cell-recycle reactor is low and a large fermenter is required. Alternatively, at a high feed rate, a high cell concentration must be maintained so as to convert all the lactose to lactic acid. At higher cell concentrations, the permeability of the cross-flow microfiltration membranes is reduced and more surface area is required to filter a unit volume of fermentation broth. Typically, feed rates of between 0.1 and 0.5 fermenter volumes per hour may be used.

The purge rate used depends on the kinetics of the fermentation for the organism selected, as it is this parameter that controls conversion in the fermenter. Typically this would be set so as to ensure at least 90% conversion of the lactose. For the *L. casei* fermentation, it is necessary to maintain the purge rate below 0.03 volumes broth per volume of fermenter per hour.

For this invention, the preferred feed rate is 0.25 fermenter volumes per hour. This gives a volumetric productivity of about 12 grams lactic acid per liter per hour. The cell mass in the fermenter is maintained at about 60 grams per liter by operating a purge stream at a rate of 0.007 volumes per hour. These conditions give 99.5% conversion of the lactose, a high volumetric productivity, and a cell concentration at which the performance of the cross-flow microfiltration device(s) (as measured by the rate of permeation) is not adversely affected.

The mode of operation of the recycle loop, which includes the selection of the recirculation pump, the rate of pumping, the selection and configuration of the cross-flow filter, the cleaning of the filter, the pressure drops around the filter and the amount of throttling of the cell broth retentate, is not important for this process. Any of the commerically available cross-flow microfiltration or high molecular weight cut-off ultrafiltration devices may be used in a manner recommended by the manufacturer without changing the conversion of the lactose to lactic acid. Alternatively a continuous centrifuge may be used to separate the cells from the cell-broth without changing the composition of the product stream pumped to the downstream purification operations.

Using the preferred fermentation conditions, it is possible to reduce the level of lactose in the product stream to less than 0.01%. Additionally, the fermentation gives this level of performance even when the concentration of lactose in the waste whey permeate stream varies by more than 10%. These characteristics are important to the overall process as it is necessary to reduce the residual level of lactose in the lactic acid product stream to as low a level as possible so as to minimize color formation during heating, a definition of heat-stable, food-grade lactic acid.

The substrate from which the lactic acid will be recovered according to the present invention may be any aqueous solution containing lactic acid. However, specifically for this invention, the substrate is a fermentation broth that may be whole, centrifuged, ultrafiltered, or otherwise prepared to remove suspended debris.

The prepared broth containing the lactic acid will be acidified to a pH in the range of about 0.5 to about 6.0. Acidification is usually required since many fermentation broths are neutral or basic. Acidification is critical since the extraction step will utilize a tertiary amine: The pH gradient between the lactic acid-containing aqueous solution and the amine-containing extracting phase drives the extraction to provide a favorable coefficient of distribution of lactic acid between the amine and aqueous phases in the extracting operation.

Acidification may be accomplished by adding mineral acids such as sulfuric, hydrochloric, and the like. Adding mineral acids increases the ionic strength of the aqueous solution which assists in breaking down emulsions which may occur between the aqueous phase and amine-containing extraction phase. Emulsions, if formed, may also be reduced or eliminated by gentle agitation or by adding salts. Such salts may be ammonium, alkali, or alkaline earth chlorides, phosphates or sulfates. Addition of mineral acids or salts to alleviate emulsions, however, should be minimized since anions from the acid and salts may be coextracted with the lactic acid.

Alternatively, and preferably, the acidification of the fermentation broth may be accomplished by passing the aqueous solution through an appropriate cation exchange resin in the hydrogen form to achieve the desired pH range. Acidification by ion exchange also has the advantage of removing undesired cations from the prepared broth and eliminates the addition of anions which may be coextracted with the lactic acid.

After adjustment of the pH within the range of 0.5 to 6.0, the solution containing the lactic acid will be extracted with a water-immiscible liquid consisting essentially of a trialkyl tertiary amine of at least 24 carbon atoms and an organic solvent. The organic solvent is characterized by a high coefficient of distribution for the lactic acid, where the coefficient of distribution is defined as the ratio of the weight fraction of lactic acid in the organic solvent to the weight fraction of the lactic acid in the aqueous phase. The organic solvent should also have low viscosity to enhance mixing of the organic solvent and aqueous phases and to minimize the power consumption required for the various mixing and pumping operations which may be utilized in mechanizing the process. The organic solvent must be water-immiscible, meaning that it should have a low solubility in water, and water should have a low solubility in the organic solvent. The organic solvent should also be substantially chemically stable to acids and bases at ambient temperatures. Therefore, in most instances, primary and secondary amines will not be desirable organic solvents for this process. Finally, the organic solvent should be environmentally acceptable if the process according to the present invention will be used on an industrial scale. Thus, while halogenated hydrocarbons may have the desirable characteristics for operability in the present invention (see FIG. 1), to conduct the process on an industrial scale, the use of halogenated hydrocarbons would not be preferred for health and environmental reasons.

The preferred class of organic solvents used in the extraction step comprises aliphatic ketones having at least 8 carbon atoms, particularly 8 to 14 carbon atoms. Ketones are preferred due to the properties of a high coefficient of distribution of lactic acid for ketone versus water, of low solubility of ketone in water or of water in ketone, and of the synergistic effect between ketone and tertiary amine in improving the coefficient of distribution of lactic acid. Particularly preferred are isobutyl-heptyl ketone and 2-octanone. Other classes of organic solvents will be operable such as aromatic hydrocarbons (e.g., toluene), alcohols of at least 8 carbon atoms (e.g., 2-ethylhexanol), esters (e.g., dibutyl phthalate), or hydrocarbon mixtures (e.g., kerosene). In addition, halogenated hydrocarbons will be useful, such as methylene chloride; however, as indicated above, for environmental reasons, they are less desirable. Surprisingly, the addition of phosphoryl oxides, such as TOPO, to the tertiary amine-solvent mixture increases the solvent capacity beyond that expected due to just the additional number of active sites.

The general conditions of the extraction step will be at ambient temperatures; however, less than ambient temperatures may be utilized, for example, to reduce emulsions, or higher than ambient temperatures may be utilized, for example, to enhance the solubilities of salts which may precipitate at low temperatures. Generally, the extraction step may be conducted, therefore, at a temperature in the range of about 0° C. to 70° C. It is important to note that the exact temperature of the extraction step is not critical to the invention.

The extraction step may be conducted by any conventional extraction liquid-phase contacting method. For example, the organic extracting phase in the aqueous solution may be mixed together in a tank of suitable size, allowed to separate into phases, and either the upper or lower phase may be drained from the tank. Alternatively, the phases may be contacted by countercurrent flow methods which are known to those of skill in the art.

The organic extracting phase according to the present invention will also contain a tertiary amine. The amines will be long carbon chain amines since it has been found that they exhibit the appropriate coefficients of distribution and are immiscible with water. In particular, tertiary amines containing at least 24 carbon atoms will be utilized. Usually a mixture of amines will be utilized since it is generally not necessary that a pure amine be used. Various mixtures of long chain amines are available, and a particularly preferred mixture of amines is the group of tri-(C8–C10)-amines, generally available under the name of Adogen 364.

The amount of tertiary amine used in the organic solvent will depend upon the particular amine and organic solvent in which the lactic acid is to be extracted, i.e., the coefficient of distribution of the lactic acid between the extraction solvent phase and the aqueous phase is a function of the amount of the particular amine used in the particular extraction solvent. Surprisingly, this relationship is not a linear function (see FIG. 1). Generally, over 50% volume of the amine will be used in the amine-organic solvent mixture.

Referring to FIG. 1, the coefficient of distribution of lactic acid between water and the organic phase consisting of Adogen 364 and an organic solvent is shown as a function of volume percent of the amine in six different solvents. Surprisingly, the concentration of amine in the solvent beyond a certain point does not result in a linear increase in the distribution coefficient of lactic acid. Also, the observed "optimal ratio" of Adogen 364 concentration to solvent concentration varies depending on the specific solvent utilized. Thus, part of this invention is that for extracting lactic acid, it is highly desirable to choose an optimum mixture of amine and solvent which produces the highest coefficient of distribution.

As can be seen in FIG. 1, methylene chloride among the solvents tested, exhibits the best coefficient of distribution; however, as discussed above, it would be undesirable in an industrial process since it is a halogenated hydrocarbon with high vapor pressure and high solubility in water. Thus, the preferred solvent is isobutyl-heptyl ketone. Again, referring to FIG. 1, a mixture of Adogen 364 in the volume percent range of about 60% to 75% in isobutyl-heptyl ketone is a preferred extraction solvent for lactic acid.

After contact of the aqueous solution containing lactic acid with the amine-containing organic extraction solvent, the two phases will be separated and the organic phase, which then contains a substantial portion of the desired lactic acid, will be subjected to a back-extraction step.

The back-extraction step will be conducted at the same or a lower temperature than the temperature at which the extraction is performed. This is because the driving force for the separation process of this invention is the pH change between the acidified broth and the back-extraction solution. Changes in temperature between the extraction step and the back-extraction step may change the coefficients of distribution *only slightly* from the values fixed by the respective pH values of the various phases in substantially isothermal extraction and back-extraction steps. Therefore, it is not necessary or desirable to change the temperature to practice this invention.

In the back-extraction step, the organic phase from the extraction step will be contacted with a basic material selected from a group consisting of aqueous ammonium hydroxide, solid alkalis, solid alkaline earth compounds, and aqueous non-homogenous suspensions of solid alkalis and solid alkaline earth compounds. This back-extraction converts the lactic acid into a salt, thereby making it soluble in an aqueous phase. Exemplary materials used in the back-extraction include aqueous solutions of sodium carbonate, sodium hydroxide, ammonium carbonate or ammonium hydroxide. Solid materials may be used such as calcium, magnesium, iron, zinc, and aluminum hydroxides, oxides, and carbonates. Aqueous suspensions of these solid materials may also be used. Preferably, aqueous ammonium hydroxide should be used because of ease of stripping ammonia from the organic phase in subsequent processing. Dispersions of calcium hydroxide are also preferred because of the ease of filtering unreacted calcium hydroxide out of the organic phase in subsequent processing.

After the back-extraction step, the aqueous phase is separated and may be subjected to such operations as may be required or desired for purifying, changing, or reconstituting it by removal of impurities and other auxiliary substances.

Referring to FIG. 2, there is shown a process flow diagram for one embodiment of the method according to the present invention. If whole whey is to be utilized as a starting material, it will be introduced through line 10 into ultrafiltration apparatus 11. The retentate from the ultrafiltraion apparatus 11 will be withdrawn through line 12 where portions of it may be recycled through line 13 or withdrawn for other uses through line 14. The permeate from which a substantial portion of the proteins over a molecular weight of 10,000 daltons have been removed by ultrafiltration device 11 will be withdrawn through line 15 for further processing.

If an ultrafiltered whey is used as a starting material, it may be directly introduced into line 15 through line 16. Optional vitamin, mineral, amino acid, or other nutrient additives may be mixed with the whey from container 17. The pH of the whey is adjusted by adding acid, or other pH adjusting reagent from tank 18. The whey is then heated by passing through heater 19, such as a steam or hot water heater, to raise the temperature appropriate for the reaction with the protease. The heated whey is then added to tank 21 through line 20 and mixed with protease introduced through line 22. The mixture will usually be agitated such as by a stirrer 23 for a period of time sufficient to proteolyze the whey while maintaining the appropriate temperature in the tank 21.

The proteolyzed whey is withdrawn through line 24 and then sterilized by filtration through device 25; heat sterilization can also be utilized. The sterilized whey permeate is then transferred through line 26 to the fermenter 27. The microorganism is introduced into the fermenter via line 28, and the pH of the fermentation broth in the fermenter 27 is maintained by adding ammonium hydroxide through line 29. Cells and lactic acid-containing fermentation broth are withdrawn through line 30, pass through pump 31, continue through line 32 to the cross-flow filtration device 33. The cell suspension is returned to the fermenter via line 34, with a purge through line 35.

The lactic acid-containing fermentation broth which has passed through the filter 33 is transferred through line 36 to the pH adjustment means 37. The pH adjustment means may either be an acidification tank, in which case a mineral acid may be introduced through line 38, or may be one or more ion exchange resins whereby the aqueous solution is adjusted to the appropriate pH range. The pH-adjusted lactic acid solution will be transferred through line 39 into forward extraction system 40, which may be a typical apparatus used for batch or continuous extraction. Fresh extraction solvent may be introduced through line 41 and regenerated extraction solvent may be introduced via line 42. The raffinate waste material may be withdrawn through line 43. The organic extract is withdrawn through line 44 and introduced into back extraction system 45. The back extraction material, which may be aqueous ammonium hydroxide, aqueous dispersion of calcium hydroxide, or other material as described above, may be introduced into back extraction system 45 through line 46. The aqueous back extract is withdrawn from system 45 through line 47 into stripping system 48. Regenerated organic solvent may be recycled through line 42 into forward extraction system 40. The stripping system 48 may be a gas stripping means in the case where the back extraction material is aqueous ammonium hydroxide. This would remove gaseous ammonia from the back extraction liquid. Alternatively, stripping system 48 may be a filtration device for filtering off excess alkali or alkaline earth material, such as calcium hydroxide where calcium hydroxide is used as a back extraction material. The stripped back extraction raffinate is then removed through line 49 into a carbon absorption apparatus 50 which removes dissolved or entrained solvents, color, and other impurities from the aqueous liquid. The lactate-containing solution is then withdrawn through line 51 where it is acidified in apparatus 52 to convert the lactate into lactic acid by conventional means such as electrodialysis, ion exchange, or chemical reaction. The extract is then subjected to polishing ion exchange apparatus 53 which consists of one or more ion exchange resins for purification, then to a final evaporator 54 where water and other volatile compounds are removed, resulting in a highly pure, heat-stable grade lactic acid recovered through line 55.

The lactic acid recovered at the completion of this process is heat-stable, as determined by refluxing it (i.e., 88% lactic acid) at 180° C. for 2 hours. The resultant liquid was then compared to APHA color standards. A reading of less than 40 was obtained which is defined as heat-stable lactic acid.

The invention is further illustrated, but not limited by the following examples:

EXAMPLE 1

Sweet cheese whey permeate (WP) was obtained from the Leprino Foods' cheese plant located in Tracy, Calif. This whey is ultrafiltered at the Leprino Foods plant using membranes with a nominal 5,0000 molecular weight cut-off. Two 100-ml aliquots were measured out, and 1 ml of corn steep liquor (CSL) added to one (WP+CSL). The pH was adjusted to 4.0 using a 2 N sulfuric acid solution and the resultant compositions placed in a 60° C. water bath. After temperature equilibration, 0.2 ml of a freshly prepared MILEZYME AFP solution (10 mg MILEZYME AFP 2000 per ml water) was added. One-ml aliquots of each preparation were removed at 2 hr intervals and added to 0.1 ml of a 55% trichloroacetic acid (TCA) solution in a 1.5 ml Eppendorf centrifuge tube. After mixing, these samples were incubated in an ice bath for 30 minutes to allow precipitation of the protein. The samples were centrifuged for 3 minutes at 10,000 x g and the supernatants decanted. The pellets were washed once in ice cold 5% TCA, resedimented, and solubilized in 0.5 N sodium hydroxide. The resultant solution was assayed for protein content using the Lowry technique, and quantified using a standard curve based on beta-lactoglobulin. The data are presented in Table I. The sample that had been hydrolyzed for 8 hours gave no precipitate when autoclaved for 20 min at 121° C.

TABLE I

| Time (hr) | mg Protein/100 ml | | % Hydrolysis | |
| --- | --- | --- | --- | --- |
| | WP | WP + CSL | WP | WP + CSL |
| 0 | 55.6 | 62.0 | 0 | 0 |
| 2 | 10.0 | 21.0 | 82.1 | 66.1 |
| 4 | 7.0 | 9.8 | 87.4 | 84.2 |
| 6 | 7.4 | 8.4 | 86.7 | 86.5 |
| 8 | 3.0 | 3.0 | 94.6 | 95.2 |

EXAMPLE 2

Whey permeate without CSL was treated for 8 hr as in Example 1 and after sterilizing by filtration through a 0.45 micron filter, inoculated with a strain of *Lactobacillus casei* found to be suitable for production of lactic acid by fermentation. Microbial growth was measured by following the absorbance of the culture at 590 nm with time. The growth rate ($\mu$, hr$^{-1}$) was calculated according to the equation $lnX = lnX_0 + ut$, where X is the biomass concentration at time, t. The 24-hour "total biomass" value ($X_m$) is shown to indicate the amount of biomass that the respective whey samples can produce. The data shown below indicate the positive effect that protease treatment of whey permeate has on allowing growth of this microorganism; that is, over a 3-fold increase in growth rate and a 9-fold increase in growth allowed.

TABLE II

| | $\mu$ (hr$^{-1}$) | Xm (A590/ml) |
| --- | --- | --- |
| Untreated WP | 0.09 | 0.15 |
| Protease treated WP | 0.32 | 0.94 |

EXAMPLE 3

The cell recycle fermenter was set-up as follows. To a 10-liter fermentation vessel was connected a variable speed pump. The outlet from this pump was then connected via a 4-way valve to a microfiltration cross-flow ceramic filter (pore size 0.2 $\mu$m, surface area 210 cm$^2$). The filter was then connected via a second 4-way valve and a 2-way ball valve to the fermenter. The return line between the 4-way valve and the fermenter was also connected to a purge pump, so that cell broth could be constantly removed from the recycle reactor. All tubing in the system was either 0.5 inch 316 stainless steel or nylon 6/6. The 4-way valves connected to a second cross-flow microfiltration or ultrafiltration device that could be separately cleaned and chemically sterilized and then connected into the recycle reactor by turning the 4-way valves. The connection to the fermentation vessel was made using flow-through quick connect fittings. These connected to pieces that were autoclaved separately and then connected in a sterile fashion to the fermentation vessel. Prior to fermentation the recycle loop was sterilized using 1% formaldehyde recirculated overnight, followed by 6% hydrogen peroxide recirculated for 2 hours. This was displaced prior to connecting to the fermenter using sterile water. The fermenter, feed and alkali addition line and the air inlet filter were heat sterilized and connected in a manner recommended by the manufacturer. Similar pumps were used to meter in the feed and pump out the permeate from the cross-flow filter at exact rates.

The pH in the fermenter was controlled through the addition of a 22% solution of ammonium hydroxide. The temperature was controlled by an internal heat exchanger within the fermenter. The pressure in the fermenter was controlled by sealing the air exit from the fermenter and then using the air pressure regulator on the air inlet. The level in the fermenter was monitored by an antifoam probe that detected when the level got too high and by the pH probe that gave an elevated reading when the liquid level fell beneath the probe. The recirculation rate in the recycle line was controlled by having a variable speed dc motor on the recirculation pump. The pressure drop accross the filter was controlled using the ball valve or changing the over-pressure in the fermenter. The total working volume of the recycle reactor was maintained at 6 liters. The volume in the fermenter was 5 liters and the hold-up volume of the recycle loop was 1 liter.

Five liters of protease-treated whey permeate (prepared as in Example 1) was placed in the fermentation vessel and autoclaved. The recycle loop and feed lines were connected, under sterile conditions) as described and the recycle pump started. After adjusting the pH to 6.3 and the temperature to 42° C. the fermenter was inoculated with a 500-ml inoculum of *Lactobacillus casei* (ATCC 11443) grown for 23 hours in LLM medium (1% bactotryptone, 2% lactose, 0.17% yeast nitrogen base, 0.05% sodium acetate). After inoculation, the feed and permeate pumps were immediately started at a dilution rate of 0.28 volumes per volume per hour. The feed was protease-treated whey permeate to which 0.5% corn steep liquor had been added. During the growth phase, a high concentration of nutrients has to be used to support the rapid growth of the cell mass. To allow the cell mass to build, initially there was no cell purge stream taken from the fermenter.

After two days, the cell density in the fermenter was 15 grams per liter and the residual lactose had decreased to less than 0.1 grams per liter. Thus more than 99.8% of the lactose added was being utilized and converted to either lactic acid, cell mass or byproducts. The corn steep liquor concentration in the feed was gradually reduced to 0.15% over the next two days. On the third day of the fermentation the purge pump was started at a rate of 0.4 ml per minute, this was increased to 0.7 ml per minute on the seventh day. The conversion of lactose still remained greater than 99.8%. The cell mass increased at a slow rate during this period.

Steady-state under these operating conditions was obtained after about 10 days of fermentation. The cell mass was between 50 and 55 grams per liter. The volumetric productivity of the fermentation was about 12 grams lactic acid per liter per hour. Thus, for example, from a feed containing 47.6 grams per liter lactose and 3.6 grams per liter lactic acid, a permeate stream containing non-detectable levels of lactose, 48.3 grams per liter lactic acid, 1.3 grams per liter acetic acid and trace levels of ethanol and formic acid was obtained. After this steady state had been reached, conditions were maintained for 3 weeks to demonstrate the stability of the fermentation with time.

While operating the fermenter over a long time period, the composition of the whey permeate varied considerably. The lactose concentration varied from week to week by as much as 10%, though the average concentration was about 45 grams per liter. Despite this, no residual levels of lactose were ever detected during the fermentation (limit of detection and quantification was 0.1 grams per liter). This is due to the very high biomass in the fermenter which is so starved of sugar that any lactose available is immediately utilized. In addition, the high biomass levels mean that any process upsets, caused for instance by leaking filtration membranes or pumps, can be fixed and the fermenter returned to complete sugar conversion very rapidly. The very low sugar levels after steady-state has been reached, in combination with the anaerobic nature of the fermentation and the relatively high temperature, discourage the growth of any contaminants that might invade the system. Indeed, a continuous fermentation was run using this system for longer than 7 months without any visable sign of contamination despite several instances during which contaminants might have entered the reactor.

EXAMPLE 4

Mixtures of Adogen 364 (a tertiary amine manufactured by Sherex) and 2-octanone containing different amounts of Adogen 364 (0, 15, 30, 50, 65, 80, and 100% by volume) were prepared by adding appropriate amounts of each component. A feed solution containing 3.997 weight percent sodium lactate was prepared by adding appropriate amounts of water and 60% sodium lactate syrup. Sulfuric acid (98%) was added to this solution to bring its pH to 1.2. A 20-ml portion of each of the solvent mixtures was placed in a 125-ml separatory funnel. A 20-ml portion of the lactate solution was added to each of the separatory funnels. The funnels were agitated on a shaker at 250 rpm for 30 minutes at room temperature and then allowed were allowed to settle for 30 minutes. The aqueous phase (raffinate) was centrifuged for 10 minutes at 2000 rpm and analyzed for lactic acid using HPLC (High Pressure Liquid Chromatography) technique. The distribution coefficient K was calculated for each case as $$K = \frac{\text{weight fraction lactic acid in the organic phase}}{\text{weight fraction lactic acid in the aqueous phase}}$$

at equilibrium. Weight fraction of lactic acid in the organic phase was calculated by material balance, knowing the lactic acid content in the feed and raffinate phases and density of solvents. The results are shown in Table III.

TABLE III

| Volume % Adogen 364 in solvent | LA* concentration in aqueous phase at equilibrium, wt % | LA* concentration in organic phase at equilibrium, wt % | K |
|---|---|---|---|
| 0 | 2.93 | 0.40 | 0.13 |
| 15 | 2.41 | 0.95 | 0.39 |
| 30 | 1.29 | 2.35 | 1.82 |
| 50 | 1.24 | 2.44 | 1.97 |
| 65 | 1.34 | 2.33 | 1.74 |
| 80 | 1.43 | 2.23 | 1.56 |
| 100 | 1.87 | 1.78 | 0.95 |

*LA refers to Lactic Acid in this and the following tables.

It can be seen from these data that the distribution coefficient for extraction of lactic acid is a strong function of the solvent composition. A strong synergistic effect is seen whereby distribution coefficients with the mixed solvent are much greater than the distribution coefficients with Adogen 364 or 2-octanone alone. The distribution coefficient is maximum at a solvent composition corresponding to 50% v/v Adogen 364+50% v/v 2-octanone.

EXAMPLE 5

Mixtures of Adogen 364 and methylene chloride containing different amounts of Adogen 364 (0, 20, 40, 60, 80% by volume) were prepared by adding appropriate amounts of each component. Feed solution containing 4.05 weight percent sodium lactate at pH 1.2 was prepared as described in Example 4. A 20-ml portion of each solvent mixture was placed in a 125-ml separatory funnel. A 20-ml portion of the lactate solution was added to each of the separatory funnels. The funnels were agitated on a shaker at 250 rpm for 30 minutes at room temperature and were then allowed to settle for 30 minutes. The aqueous phase (raffinate) was centrifuged for 10 minutes at 2000 rpm and analyzed for lactic acid using HPLC. Weight fraction of lactic acid in the organic phase and the distribution coefficient, $K_D$, were calculated as described in Example 4. The results are summarized below.

TABLE IV

| Volume % Adogen 364 in solvent | LA concentration in aqueous phase at equilibrium, wt % | LA concentration in organic phase at equilibrium, wt % | $K_D$ |
|---|---|---|---|
| 0 | 3.22 | 0 | 0 |
| 20 | 1.80 | 1.77 | 0.65 |
| 40 | 0.69 | 2.30 | 3.33 |
| 60 | 0.97 | 2.25 | 2.32 |
| 80 | 1.18 | 2.29 | 1.94 |

It can be seen from these data that with methylene chloride as diluent, also, the distribution coefficient for extraction of lactic acid is a strong function of the relative proportion of Adogen 364 and methylene chloride in the solvent. The distribution coefficient with the mixed solvent is much greater than that for Adogen 364 (see Example 4) or methylene chloride alone. The distribution coefficient is maximum at a solvent composition corresponding to 40% v/v Adogen 364+60% v/v methylene chloride. Comparison of the results in Examples 4 and 5 indicates that the maximum distribution coefficient using methylene chloride as diluent (3.33) is much larger than the maximum distribution coefficient using 2-octanone as diluent (1.97).

EXAMPLE 6

Mixtures of Adogen 364 and a diluent (isobutyl-heptyl ketone [IBHK], toluene, or dibutyl phthalate) containing different amounts of Adogen 364 were prepared by adding appropriate amounts of each component. The feed solution was supernatant from the fermentation broth containing 3.12 weight percent lactic acid, after adjusting the pH to 1.2 by addition of 98% sulfuric acid. The procedure described in Example 4 was used to carry out the extraction experiments. No precipitation of proteinaceous material was seen upon contact between the organic solvent and fermentation broth, unless the cheese whey permeate had not been submitted to protease treatment prior to fermentation. Further results are summarized in Table V.

TABLE V

| Diluent | Volume % Adogen 364 in mixed solvent | wt % LA in aqueous phase at equilibrium | wt % LA in organic phase at equilibrium | $K_D$ |
|---|---|---|---|---|
| IBHK | 0 | 3.04 | 0.09 | 0.03 |
|  | 20 | 2.31 | 0.99 | 0.43 |
|  | 40 | 1.34 | 2.22 | 1.66 |
|  | 60 | 1.07 | 2.61 | 2.44 |
|  | 80 | 1.09 | 2.58 | 2.37 |
| Toluene | 0 | 3.12 | 0 | 0 |
|  | 20 | 2.20 | 1.08 | 0.49 |
|  | 40 | 1.41 | 2.06 | 1.46 |
|  | 60 | 1.19 | 2.38 | 2.00 |
|  | 80 | 1.11 | 2.54 | 2.29 |
| Dibutyl phthalate | 0 | 3.12 | 0 | 0 |
|  | 20 | 1.75 | 1.40 | 0.80 |
|  | 40 | 1.32 | 1.91 | 1.45 |
|  | 60 | 1.43 | 1.92 | 1.34 |
|  | 80 | 1.55 | 1.89 | 1.22 |

These data show that IBHK gives a maximum distribution coefficient of 2.44 at the solvent composition 60% v/v Adogen +40% v/v IBHK. The low solubility of IBHK in the aqueous phase also makes it a preferred diluent.

EXAMPLE 7

By adding appropriate amounts of the two components, mixtures of Adogen 364 and IBHK were prepared to make:
(a) 60% v/v Adogen 364+40% v/v/IBHK,
(b) 40% v/v Adogen 364+60% v/v IBHK, and
(c) 100% IBHK.
To each of these solvent mixtures different amounts of TOPO (trioctyl phosphoryl oxide), sold by Kodak, were added to make solutions containing, respectively, 5, 10, 15, and 20 weight percent TOPO in each of the three mixtures described above, namely (a), (b), and (c). Aqueous feed for the extraction experiments was cation and anion exchanged fermentation broth supernatant containing 3.58 weight percent lactic acid. In separatory funnels, 20 ml of aqueous feed and 20 ml of the solvent mixture was added, and extractions and analysis was done as described in Example 4. The results are summarized in Table VI.

TABLE VI

| wt % TOPO | Composition of solvent before adding TOPO | wt % LA in aqueous phase at equilibrium | wt % LA in organic phase at equilibrium | $K_D$ |
|---|---|---|---|---|
| 0 | 60% v/v Adogen 364 + 40% v/v IBHK | 1.41 | 2.71 | 1.92 |
| 5.0 | 60% v/v Adogen 364 + 40% v/v IBHK | 1.23 | 2.93 | 2.38 |
| 10.0 | 60% v/v Adogen 364 + 40% v/v IBHK | 1.13 | 3.01 | 2.66 |
| 14.4 | 60% v/v Adogen 364 + 40% v/v IBHK | 1.00 | 3.15 | 3.15 |
| 20.0 | 60% v/v Adogen 364 + 40% v/v IBHK | 0.90 | 3.24 | 3.60 |
| 0 | 40% v/v Adogen 364 + 60% v/v IBHK | 1.61 | 2.38 | 1.48 |
| 5.0 | 40% v/v Adogen 364 + 60% v/v IBHK | 1.36 | 2.71 | 1.99 |
| 9.8 | 40% v/v Adogen 364 + 60% v/v IBHK | 1.31 | 2.75 | 2.10 |
| 20.0 | 40% v/v Adogen 364 + 60% v/v IBHK | 1.08 | 3.01 | 2.79 |
| 0 | 100% v/v IBHK | 3.46 | 0.90 | 0.26 |
| 5.0 | 100% v/v IBHK | 3.12 | 0.69 | 0.22 |
| 10.2 | 100% v/v IBHK | 2.99 | 0.84 | 0.28 |
| 14.9 | 100% v/v IBHK | 2.73 | 1.15 | 0.42 |
| 20.0 | 100% v/v IBHK | 2.39 | 1.53 | 0.64 |

These data shown that addition of TOPO to the tertiary amine-ketone mixture greatly increases the distribution coefficient. The increase in distribution coefficient is greater at higher tertiary amine content. TOPO and ketone mixtures alone give much lower distribution coefficients.

EXAMPLE 8

A sample of 650 ml of cation and anion exchanged supernatant from a fermentation broth containing 4.18 weight percent lactic acid pH 2.1 was contacted with 250 ml solvent (60% v/v Adogen 364+40% v/v IBHK). The mixture was shaken vigorously by hand for 10 minutes and allowed to settle for 16 hours. The loaded solvent was pipetted off. Lactic acid content in the loaded solvent was measured in the following manner. Ten ml of loaded solvent was mixed with 30 ml 10 weight percent sodium hydroxide solution in a separatory funnel. The mixture was agitated in a shaker at 250 rpm for 30 minutes and settled for 1 hour. The aqueous phase was centrifuged and analyzed for lactic acid. It contained 1.71 gram lactic acid per 100 ml solution. Thus, the lactic acid content in the loaded solvent was calculated by mass balance to be 5.13 gram lactic acid per 100 ml solvent.

In separatory funnels, 30 ml loaded solvent was added to 10 ml ammonia solutions. The ammonia concentrations were varied from 1.45 to 4.37 weight percent to give stoichiometric ratios (gram equivalent ammonia per gram equivalent ammonia lactic acid) that ranged from 0.5 to 1.5. Back-extractions were carried out by agitating the mixture at 250 rpm for 30 minutes, settling the mixture for 1 hour and centrifuging the aqueous phase. The aqueous phase was analyzed for lactic acid content by HPLC and percent regeneration of the loaded solvent was calculated as grams lactic acid in ammonia solution per grams lactic acid in the initial loaded solvent. The distribution coefficient for back-extraction, $K_w$, was defined as $$K_w = \frac{\text{weight fraction lactic acid in aqueous phase}}{\text{weight fraction lactic acid in regenerated solvent}}$$

at equilibrium. The results are summarized in Table VII.

TABLE VII

| Stoichiometric Ratio | wt % ammonia in initial aqueous phase | wt % LA in aqueous phase at equilibrium | wt % LA in organic phase at equilibrium | % Regeneration of solvent | $K_w$ |
| --- | --- | --- | --- | --- | --- |
| 0.50 | 1.45 | 6.89 | 3.49 | 44.8 | 1.98 |
| 0.75 | 2.18 | 9.60 | 2.38 | 62.4 | 4.04 |
| 1.00 | 2.91 | 11.39 | 1.64 | 74.0 | 6.93 |
| 1.20 | 3.49 | 13.23 | 0.89 | 86.0 | 14.95 |
| 1.50 | 4.37 | 12.80 | 1.07 | 83.1 | 12.00 |

These data indicated that no increase in temperature is required for efficient back-extraction of lactic acid.

These data also indicate that the solvent is regenerable by ammonia solutions. Using a solvent-to-aqueous ratio of 3 results in a more concentrated lactic acid solution. In a single stage contact, more than 80% solvent regeneration is achieved, with a slightly greater than stoichiometric amount of ammonia. Thus, complete solvent regeneration is accomplished using 2 or 3 stages and countercurrent operation at slightly greater than stoichiometric ammonia.

EXAMPLE 9

A sample of 650 ml of cation and anion exchanged supernatant from fermentation broth was contacted with 250 ml solvent (60% v/v Adogen 364+40% v/v IBHK). Extraction was carried out and lactic acid content in the loaded solvent was measured using the procedure described in Example 8. Lactic acid content in the loaded solvent was found to be 5 gram per 100 ml solvent. In separatory funnels, 30 ml loaded solvent was added to 10 ml calcium hydroxide slurry. The concentration of calcium hydroxide was varied over the range of 3.09 to 9.26 weight percent to give stoichiometric ratios (gram equivalent calcium hydroxide per gram equivalent lactic acid) that ranged from 0.5 to 1.5. Back extractions were carried out as described in Example 8. The lactic acid content of the regenerated solvent was determined by contacting the solvent with 30 ml 10 weight percent sodium hydroxide solution and then analyzing the sodium hydroxide solution for lactic acid. Lactic acid content of the calcium hydroxide slurry was determined knowing the lactic acid content of the solvent before and after back extraction and carrying out a material balance. Results are summarized in Table VIII.

TABLE VIII

| Stoichiometric Ratio | wt % Ca(OH)$_2$ in initial aqueous phase | wt % LA in aqueous phase at equilibrium | wt % LA in organic phase at equilibrium | % Regeneration of solvent | $K_w$ |
| --- | --- | --- | --- | --- | --- |
| 0.50 | 3.09 | 2.98 | 7.51 | 51.6 | 2.52 |
| 0.75 | 4.63 | 1.65 | 10.50 | 73.2 | 6.36 |
| 1.00 | 6.77 | 0.42 | 13.17 | 93.2 | 31.40 |
| 1.50 | 9.26 | 0 | 13.73 | 100.0 | ∞ |

These data indicate that solvent is regenerable by calcium hydroxide slurry. Using a solvent-to-aqueous ratio of 3 results in a more concentrated lactic acid solution. In a single stage contact, complete solvent regeneration is achieved by using 1.5 times the stoichiometric amount of calcium hydroxide and a solvent to calcium hydroxide slurry ratio of 3 v/v.

EXAMPLE 10

Mixtures of Adogen 364 and IBHK or 2-octanone, each containing a proportion of 60% Adogen to 40% diluent were prepared by adding the appropriate amounts of each component. Feed solution containing the indicated grams per liter lactose was added to the Adogen/diluent mixture and extraction carried out as described in Example 4. The raffinate was analyzed for lactose content by the DNS assay, as described in *Anal. Biochem.* 2:127–132 (1960). The concentration of lactose in the loaded solvent was determined by the difference between lactose concentrations in the raffinate and original feed.

TABLE IX

|  | g/l lactose in feed | g/l lactose in loaded solvent |
| --- | --- | --- |
| 60% v/v Adogen 364 + 40% v/v IBHK | 14.62 | 0 |
| 60% v/v Adogen 364 + 40% 2-octanone | 31.00 | 0.46 |

These results demonstrate that the organic extraction solutions (i.e., Adogen 364 mixed in proper proportion with IBHK or 2-octanone) utilized in the invention to extract lactic acid also have the property of efficiently excluding lactose. Adogen 364 mixed with IBHK works better than does Adogen 364 mixed with 2-octanone.

What is claimed is:

1. A process for producing lactic acid from a carbohydrate-containing medium comprising the steps of:
    (a) fermenting said carbohydrate-containing medium with a lactic acid or lactic acid salt-producing microorganism in a fermentation ot form a broth;
    (b) continuously removing a product-containing both from said zone, removing cells of said microorganism from said broth to form a cell-free product-containing stream and recycling said cells to said zone;
    (c) contacting said cell-free product-containing stream at an acidic pH with a water-immiscible liquid consisting essentially of trialkyl tertiary amines of at least 24 carbon atoms and a water-immiscible organic solvent for a period of time and at a temperature sufficient to extract lactic acid and lactic acid salt from said stream into a water-immiscible phase, said liquid characterized by a distribution coefficient in excess of 1.0 for lactic acid and lactic acid salt in said liquid versus water;
    (d) separating said water-immiscible phase from the mixture formed in step (c);
    (e) contacting said water-immiscible liquid from step (d) with a material selected from the group consisting of aqueous ammonium hydroxide, solid alkalis, solid alkaline earth compounds, and aqueous non-homogenous suspensions of solid alkalis or solid alkaline earth compounds, whereby lactic acid and lactic acid salt are removed from said water-immiscible phase.

2. A process for producing lactic acid from a carbohydrate-containing medium comprising the steps of:
(a) fermenting said carbohydrate-containing medium with a lactic acid or lactic acid salt-producing microorganism in a fermentation zone;
(b) removing a product-containing both from said zone, removing cells of said microorganism from said broth to form a cell-free product-containing stream;
(c) contacting said cell-free product-containing stream at an acidic pH with a water-immiscible liquid consisting essentially of trialkyl tertiary amines of at least 24 carbon atoms and a water-immiscible organic solvent for a period of time and at a temperature sufficient to extract lactic acid and lactic acid salt from said stream into a water-immiscible phase, said liquid characterized by a distribution coefficient in excess of 1.0 for lactic acid and lactic acid salt in said liquid versus water;
(d) separating said water-immiscible phase from the mixture formed in step (c);
(e) contacting said water-immiscible liquid from step (d) with a material selected from the group consisting of aqueous ammonium hydroxide, solid alkalis, solid alkaline earth compounds, and aqueous non-homogenous suspensions of solid alkalis or solid alkaline earth compounds, whereby lactic acid and lactic acid salt are removed from said water-immiscible phase.

3. A process according to claim 1 or 2 wherein in step (a) said lactic acid or lactic acid salt-producing microorganism is a microorganism that produces primarily D(−)lactic acid or lactate, L(+)lactic acid or lactate, or a D(−)L(+) racemic mixture of lactic acid or lactate.

4. A process according to claim 1 or 2 wherein in step (a) said lactic acid or lactic acid salt-producing microorganism is a species selected from the genus Lactobacillus or Streptococcus.

5. A process according to claim 1 or 2 wherein in step (b) said removal of said cells from said broth is accomplished by cross-flow microfiltration.

6. A process according to claim 1 or 2 wherein in step (b) said removal of said cells from said broth is accomplished by ultrafiltration with a filter whose molecular weight cutoff is greater than 100,000.

7. A process according to claim 1 or 2 wherein in step (b) said removal of said cells from said broth is accomplished by centrifugation.

8. A process according to claim 1 or 2 further comprising the step of increasing the ionic salt concentration of said aqueous solution prior to step (c) by adding a salt selected from the group consisting of chlorides, phosphates and sulfates of ammonium, alkali, metals and alkaline earth metals.

9. A process according to claim 1 or 2 wherein in step (c) said product-containing stream is at a pH in the range of 0.5 to 6.0.

10. A process according to claim 1 or 2 wherein in step (c) said water-immiscible organic solvent is selected from the group consisting of C8 to C14 aliphatic ketones and halogenated hydrocarbons.

11. A process according to claim 1 or 2 wherein in step (e) said material comprises aqueous ammonium hydroxide.

12. A process according to claim 1 or 2 wherein said step (e) comprises contacting said water immiscible phase with solid alkali or alkaline earth compound.

13. A process according to claim 12 wherein said alkali or alkaline earth compound is selected from the group consisting of hydroxides, oxides and carbonates of calcium, magnesium, iron, zinc, and aluminum.

14. A process according to claim 1 or 2 further comprising the step of, prior to said step (c), contacting said stream with an ion exchange resin to adjust said stream to a pH in the range of 0.5 to 6.0.

15. A process according to claim 1 or 2 wherein in step (c) said tertiary amine comprises a trialkyl amine and said solvent comprises isobutyl-heptyl ketone.

16. A process according to claim 1 or 2 wherein in step (c) said tertiary amine comprises a trialkyl amine and said solvent comprises 2-octanone.

17. A process according to claim 15 wherein said step (e) comprises contacting said water-immiscible phase with aqueous ammonium hydroxide.

18. A process according to claim 15 wherein said step (e) comprises contacting said water-immiscible phase with said aqueous suspension of said alkali or alkaline earth compound.

19. A process according to claim 1 or 2 wherein in step (c) said tertiary amine comprises a trialkyl amine and said solvent comprises a mixture of a ketone and a phosphoryl oxide.

20. A process according to claim 1 or 2 wherein in said step (e) said contact occurs at the same or at a lower temperature than the temperature at which the extraction step (c) is performed.

21. A process according to claim 1 or 2 wherein said lactic acid is heat-stable.

* * * * *